(12) United States Patent
D'Ambrosio

(10) Patent No.: US 9,002,469 B2
(45) Date of Patent: Apr. 7, 2015

(54) TRANSCUTANEOUS ENERGY TRANSFER SYSTEM WITH MULTIPLE SECONDARY COILS

(75) Inventor: Ralph L. D'Ambrosio, Wenham, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 13/328,582

(22) Filed: Dec. 16, 2011

(65) Prior Publication Data

US 2012/0157753 A1    Jun. 21, 2012

Related U.S. Application Data

(60) Provisional application No. 61/425,159, filed on Dec. 20, 2010.

(51) Int. Cl.
| | | |
|---|---|---|
| *A61N 1/08* | (2006.01) | |
| *A61M 1/12* | (2006.01) | |
| *H02J 7/02* | (2006.01) | |

(52) U.S. Cl.
CPC ............ *A61M 1/127* (2013.01); *H02J 7/025* (2013.01); *A61M 1/122* (2014.02); *A61M 2205/18* (2013.01); *A61M 2205/8206* (2013.01); *A61M 2205/8243* (2013.01)

(58) Field of Classification Search
None
See application file for complete search history.

(56) References Cited

U.S. PATENT DOCUMENTS

| | | |
|---|---|---|
| 3,195,038 A | 7/1965 | Fry |
| 3,195,540 A | 7/1965 | Waller |
| 3,357,432 A | 12/1967 | Sparks |
| 3,357,434 A | 12/1967 | Abell |
| 3,711,747 A | 1/1973 | Sahara et al. |
| 3,756,246 A | 9/1973 | Thaler et al. |
| 3,824,129 A | 7/1974 | Fagan, Jr. |
| 3,825,925 A | 7/1974 | Drusch |
| 3,866,616 A | 2/1975 | Purdy et al. |
| 3,867,950 A | 2/1975 | Fischell |
| 3,888,260 A | 6/1975 | Fischell |
| 3,915,038 A | 10/1975 | Malin |
| 3,934,177 A | 1/1976 | Horbach |
| 3,942,535 A | 3/1976 | Schulman |

(Continued)

FOREIGN PATENT DOCUMENTS

| | | |
|---|---|---|
| DE | 2720011 A1 | 11/1978 |
| EP | 0 507 360 A2 | 10/1992 |

(Continued)

OTHER PUBLICATIONS

[No Author Listed] SBS 1.1—Compliant Gas Gauge and Protection Enabled with Impedance Track™, Texas Instruments, SLUS757B—Jul. 2007, Revised Apr. 2008. 18 pages.

(Continued)

*Primary Examiner* — Brian T Gedeon
*Assistant Examiner* — Ankit Tejani
(74) *Attorney, Agent, or Firm* — Thomas J. Engellenner; Reza Mollaaghababa; Pepper Hamilton LLP

(57) ABSTRACT

A transcutaneous energy transfer (TET) system is provided having a plurality of secondary coils adapted for disposition in a patient, at least one primary coil configured to transmit transcutaneous energy, and a controller adapted for disposition in a patient. The controller includes circuitry to isolate the secondary coils from each other and direct electric current from at least one of the secondary coils to a charge storage device and/or implantable medical device.

15 Claims, 6 Drawing Sheets

(56) References Cited

U.S. PATENT DOCUMENTS

| | | |
|---|---|---|
| 3,987,799 A | 10/1976 | Purdy et al. |
| 3,995,137 A | 11/1976 | Okada et al. |
| 4,011,499 A | 3/1977 | Betsill et al. |
| 4,012,769 A | 3/1977 | Edwards et al. |
| 4,041,955 A | 8/1977 | Kelly et al. |
| 4,068,292 A | 1/1978 | Berry et al. |
| 4,071,032 A | 1/1978 | Schulman |
| 4,104,701 A | 8/1978 | Baranowski |
| 4,134,408 A | 1/1979 | Brownlee et al. |
| 4,143,661 A | 3/1979 | LaForge et al. |
| 4,186,749 A | 2/1980 | Fryer |
| 4,266,533 A | 5/1981 | Ryaby et al. |
| 4,441,210 A | 4/1984 | Hochmair et al. |
| 4,441,498 A | 4/1984 | Nordling |
| 4,517,585 A | 5/1985 | Ridout et al. |
| 4,539,433 A | 9/1985 | Ishino et al. |
| 4,586,508 A | 5/1986 | Batina et al. |
| 4,665,896 A | 5/1987 | LaForge et al. |
| 4,673,888 A | 6/1987 | Engelmann et al. |
| 4,678,986 A | 7/1987 | Barthelemy |
| 4,679,560 A | 7/1987 | Galbraith |
| 4,716,353 A | 12/1987 | Engelmann |
| 4,717,889 A | 1/1988 | Engelmann |
| 4,741,339 A | 5/1988 | Harrison et al. |
| 4,808,924 A | 2/1989 | Cecco et al. |
| 4,837,497 A | 6/1989 | Leibovich |
| 4,924,171 A | 5/1990 | Baba et al. |
| 4,925,443 A | 5/1990 | Heilman et al. |
| 4,944,299 A | 7/1990 | Silvian |
| 5,000,178 A | 3/1991 | Griffith |
| 5,004,489 A | 4/1991 | Rotman |
| 5,109,843 A | 5/1992 | Melvin et al. |
| 5,214,392 A | 5/1993 | Kobayashi et al. |
| 5,312,439 A | 5/1994 | Loeb |
| 5,314,453 A | 5/1994 | Jeutter |
| 5,324,316 A | 6/1994 | Schulman et al. |
| 5,350,411 A | 9/1994 | Ryan et al. |
| 5,350,413 A | 9/1994 | Miller et al. |
| 5,355,296 A | 10/1994 | Kuo et al. |
| 5,358,514 A | 10/1994 | Schulman et al. |
| 5,383,912 A | 1/1995 | Cox et al. |
| 5,411,536 A | 5/1995 | Armstrong |
| 5,411,537 A | 5/1995 | Munshi et al. |
| 5,480,415 A | 1/1996 | Cox et al. |
| 5,506,503 A | 4/1996 | Cecco et al. |
| 5,527,348 A | 6/1996 | Winkler et al. |
| 5,545,191 A | 8/1996 | Mann et al. |
| 5,556,421 A | 9/1996 | Prutchi et al. |
| 5,569,156 A | 10/1996 | Mussivand |
| 5,613,935 A | 3/1997 | Jarvik |
| 5,621,369 A | 4/1997 | Gardner et al. |
| 5,630,836 A | 5/1997 | Prem et al. |
| 5,690,693 A | 11/1997 | Wang et al. |
| 5,702,431 A | 12/1997 | Wang et al. |
| 5,713,939 A | 2/1998 | Nedungadi et al. |
| 5,722,998 A | 3/1998 | Prutchi et al. |
| 5,730,125 A | 3/1998 | Prutchi et al. |
| 5,733,313 A | 3/1998 | Barreras, Sr. et al. |
| 5,735,887 A | 4/1998 | Barreras, Sr. et al. |
| 5,740,257 A | 4/1998 | Marcus |
| 5,741,316 A | 4/1998 | Chen et al. |
| 5,749,909 A | 5/1998 | Schroeppel et al. |
| 5,755,748 A | 5/1998 | Borza et al. |
| 5,861,019 A | 1/1999 | Sun et al. |
| 5,948,006 A | 9/1999 | Mann |
| 5,951,459 A | 9/1999 | Blackwell |
| 5,959,522 A | 9/1999 | Andrews |
| 5,963,132 A | 10/1999 | Yoakum |
| 5,978,713 A | 11/1999 | Prutchi et al. |
| 5,991,665 A | 11/1999 | Wang et al. |
| 5,995,874 A | 11/1999 | Borza et al. |
| 6,047,214 A | 4/2000 | Mueller et al. |
| 6,048,601 A | 4/2000 | Yahagi et al. |
| 6,058,330 A | 5/2000 | Borza et al. |
| 6,067,474 A | 5/2000 | Schulman et al. |
| 6,141,592 A | 10/2000 | Pauly |
| 6,144,841 A | 11/2000 | Feeney |
| 6,149,683 A | 11/2000 | Lancisi et al. |
| 6,212,430 B1 | 4/2001 | Kung |
| 6,243,608 B1 | 6/2001 | Pauly et al. |
| 6,275,737 B1 | 8/2001 | Mann |
| 6,278,258 B1 | 8/2001 | Echarri et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,349,234 B2 | 2/2002 | Pauly et al. |
| 6,366,817 B1 | 4/2002 | Kung |
| 6,389,318 B1 | 5/2002 | Zarinetchi et al. |
| 6,395,027 B1 | 5/2002 | Snyder |
| 6,400,991 B1 | 6/2002 | Kung |
| 6,415,186 B1 | 7/2002 | Chim et al. |
| 6,430,444 B1 | 8/2002 | Borza et al. |
| 6,442,434 B1 | 8/2002 | Zarinetchi et al. |
| 6,443,891 B1 | 9/2002 | Grevious |
| 6,445,956 B1 | 9/2002 | Laird et al. |
| 6,478,820 B1 | 11/2002 | Weiss |
| 6,496,733 B2 | 12/2002 | Zarinetchi et al. |
| 6,507,759 B1 | 1/2003 | Prutchi et al. |
| 6,542,777 B1 | 4/2003 | Griffith et al. |
| 6,553,263 B1 | 4/2003 | Meadows et al. |
| 6,591,139 B2 | 7/2003 | Loftin et al. |
| 6,631,296 B1 | 10/2003 | Parramon et al. |
| 6,745,077 B1 | 6/2004 | Griffith et al. |
| 6,748,273 B1 | 6/2004 | Obel et al. |
| 6,772,011 B2 | 8/2004 | Dolgin |
| 6,959,213 B2 | 10/2005 | Prutchi et al. |
| 6,959,217 B2 | 10/2005 | DelMain et al. |
| 6,968,234 B2 | 11/2005 | Stokes |
| 7,015,769 B2 | 3/2006 | Schulman et al. |
| 7,027,871 B2 * | 4/2006 | Burnes et al. ................ 607/60 |
| 7,062,331 B2 | 6/2006 | Zarinetchi et al. |
| 7,076,304 B2 | 7/2006 | Thompson |
| 7,079,901 B1 | 7/2006 | Loftin et al. |
| 7,092,762 B1 | 8/2006 | Loftin et al. |
| 7,151,914 B2 | 12/2006 | Brewer |
| 7,155,291 B2 | 12/2006 | Zarinetchi et al. |
| 7,177,690 B2 | 2/2007 | Woods et al. |
| 7,184,836 B1 | 2/2007 | Meadows et al. |
| 7,191,007 B2 | 3/2007 | Desai et al. |
| 7,225,032 B2 | 5/2007 | Schmeling et al. |
| 7,237,712 B2 | 7/2007 | DeRocco et al. |
| 7,248,929 B2 | 7/2007 | Meadows et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,308,316 B2 | 12/2007 | Schommer |
| 7,418,297 B2 | 8/2008 | Bornhoft et al. |
| 7,437,644 B2 | 10/2008 | Ginggen et al. |
| 7,471,986 B2 | 12/2008 | Hatlestad |
| 7,482,783 B2 | 1/2009 | Schommer |
| 7,512,443 B2 | 3/2009 | Phillips et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,599,743 B2 | 10/2009 | Hassler, Jr. et al. |
| 7,599,744 B2 | 10/2009 | Giordano et al. |
| 7,632,235 B1 | 12/2009 | Karicheria et al. |
| 7,658,196 B2 | 2/2010 | Ferreri et al. |
| 7,689,176 B2 | 3/2010 | Crivelli |
| 7,711,435 B2 | 5/2010 | Schommer |
| 7,738,965 B2 | 6/2010 | Phillips et al. |
| 7,751,899 B1 | 7/2010 | Karunasiri |
| 7,751,902 B1 | 7/2010 | Karunasiri |
| 7,775,444 B2 | 8/2010 | DeRocco et al. |
| 7,813,801 B2 | 10/2010 | Youker et al. |
| 7,818,068 B2 | 10/2010 | Meadows et al. |
| 7,822,480 B2 | 10/2010 | Park et al. |
| 7,848,814 B2 | 12/2010 | Torgerson et al. |
| 7,856,986 B2 | 12/2010 | Darley |
| 2002/0016568 A1 | 2/2002 | Lebel et al. |
| 2003/0065366 A1 | 4/2003 | Merritt et al. |
| 2003/0088295 A1 | 5/2003 | Cox |
| 2003/0163020 A1 | 8/2003 | Frazier |

(56) References Cited

U.S. PATENT DOCUMENTS

| | | |
|---|---|---|
| 2003/0171792 A1 | 9/2003 | Zarinetchi et al. |
| 2004/0039423 A1 | 2/2004 | Dolgin |
| 2005/0075693 A1 | 4/2005 | Toy et al. |
| 2005/0075696 A1 | 4/2005 | Forsberg et al. |
| 2005/0107847 A1 | 5/2005 | Gruber et al. |
| 2005/0113887 A1 | 5/2005 | Bauhahn et al. |
| 2005/0288739 A1 | 12/2005 | Hassler et al. |
| 2005/0288740 A1 | 12/2005 | Hassler et al. |
| 2005/0288743 A1 | 12/2005 | Ahn et al. |
| 2006/0020300 A1 | 1/2006 | Nghiem et al. |
| 2006/0020305 A1 | 1/2006 | Desai et al. |
| 2006/0107148 A1 | 5/2006 | Ginggen et al. |
| 2006/0197494 A1 | 9/2006 | Schommer |
| 2006/0247737 A1 | 11/2006 | Olson et al. |
| 2007/0049983 A1 | 3/2007 | Freeberg |
| 2007/0106274 A1 | 5/2007 | Ayre et al. |
| 2007/0142696 A1 | 6/2007 | Crosby et al. |
| 2007/0255349 A1 | 11/2007 | Torgerson et al. |
| 2007/0270921 A1 | 11/2007 | Strother et al. |
| 2008/0027500 A1 | 1/2008 | Chen |
| 2008/0027513 A1 | 1/2008 | Carbunaru |
| 2008/0065290 A1 | 3/2008 | Breed et al. |
| 2008/0129517 A1 | 6/2008 | Crosby et al. |
| 2008/0167531 A1 | 7/2008 | McDermott |
| 2008/0312852 A1 | 12/2008 | Maack |
| 2009/0069869 A1 | 3/2009 | Stouffer et al. |
| 2009/0157148 A1 | 6/2009 | Phillips et al. |
| 2009/0273349 A1 | 11/2009 | Rondoni et al. |
| 2009/0276016 A1* | 11/2009 | Phillips et al. ............... 607/61 |
| 2010/0063347 A1 | 3/2010 | Yomtov et al. |
| 2010/0076524 A1 | 3/2010 | Forsberg et al. |
| 2010/0080025 A1 | 4/2010 | Terlizzi et al. |
| 2010/0222848 A1 | 9/2010 | Forsell |
| 2010/0305662 A1 | 12/2010 | Ozawa et al. |
| 2010/0312188 A1 | 12/2010 | Robertson et al. |
| 2011/0009924 A1 | 1/2011 | Meskens |
| 2011/0101790 A1 | 5/2011 | Budgett |
| 2011/0160516 A1 | 6/2011 | Dague et al. |
| 2011/0196452 A1 | 8/2011 | Forsell |
| 2011/0278948 A1 | 11/2011 | Forsell |
| 2012/0154143 A1 | 6/2012 | D'Ambrosio |
| 2012/0157754 A1 | 6/2012 | D'Ambrosio |
| 2012/0157755 A1 | 6/2012 | D'Ambrosio |
| 2012/0265003 A1 | 10/2012 | D'Ambrosio et al. |
| 2013/0158631 A1 | 6/2013 | Shea et al. |

FOREIGN PATENT DOCUMENTS

| | | |
|---|---|---|
| JP | 07-046164 A | 2/1995 |
| JP | H10215530 A | 8/1998 |
| JP | H10258129 A | 9/1998 |
| JP | 2002034169 A | 1/2002 |
| JP | 2010284065 A | 12/2010 |
| WO | 97/29802 A2 | 8/1997 |
| WO | 97/47065 A1 | 12/1997 |
| WO | 99/44684 A1 | 9/1999 |
| WO | 2006096685 A1 | 9/2006 |
| WO | 2008/106717 A1 | 9/2008 |
| WO | 2011008163 A1 | 1/2011 |

OTHER PUBLICATIONS

[No Author Listed] Low-power SoC (system-on-chip) with MCU, memory sub-1 ghz RF transceiver, and USB controller. TIRF Common Spec (CC1110Fx/CC1111Fx), Texas Instruments, Jul. 20, 2010, 247 pages.

[No Author Listed]Battery Spec NCR 18650. NNP Series. Panasonic. Feb. 2010, 1 page.

Abe et al., Development of transcutaneous energy transmission system for totally implantable artificial heart. Artificial Heart 2/Proceedings of the 2nd International Symposium on Artificial Heart and Assist Device. Akutsu, T. ed, Springer-Verlag, Tokyo, pp. 257-261, 1988.

Ahn et al., In Vivo Performance Evaluation of a Transcutaneous Energy and Information Transmission System for the Total Artificial Heart, ASAIO Journal 1993, M208-M212.

Barsukov, Theory and Implementation of Impedance Track™ Battery Fuel-Gauging Algorithm in bq20z8x Product Family, Texas Instruments, SLUA364, Nov. 2005. 8 pages.

Bearnson et al., Electronics Development for the Utah Electrohydrolic Total Artificial Heart. Sixth Annual IEEE Symposium on Computer-Based Medical Systems, 247-252 (1993).

Callewaert et al., A Programmable Implantable Stimulator with Percutaneous Optical Control. Ninth Annual Conference of the Engineering in Medicine and Biology Society IEEE, 1370-1371 (1987).

Davies et al., Adaptation of Tissue to a Chronic Heat Load, ASAIO Journal. 40(3), M514-7 (1994).

Donaldson, Nde N, Use of feedback with voltage regulators for implants powered by coupled coils. Med Biol Eng Comput. May 1985;23(3):291, XP002066875, ISSN: 0140-0118.

Fraim et al. Performance of a tuned ferrite core transcutaneous transformer. IEEE Trans Bio-med Eng. Sep. 1971; BME-18(5):352-9.

Galbraith et al, A Wide-Band Efficient Inductive Transdermal Power and Data Link with Coupling Insensitive Gain. IEEE Transactions on Biomedical Engineering, BME 34(4):265-275 (1987).

Geselowitz et al., The effects of metals on a transcutaneous energy transmission system. IEEE Transactions on Biomedical Engineering. vol. 39(9), pp. 928-934, Sep. 1992.

International Search Report and Written Opinion for Application No. PCT/US2011/065446, mailed Jun. 29, 2012. (10 pages).

Masuzawa, T., et al., Set-up, Improvement, and Evaluation of an Electrohydraulic Total Artificial Heart with a Separately Placed Energy Converter. (1996) ASAIO Journal, vol. 42; M328-M332.

Matsuki et al. Energy Transferring System Reducing Temperature Rise for Implantable Power Consuming Devices. Proceedings of the 18th Annual Conference of the IEEE Engineering in Medicine and Biology Society, Amsterdam Oct. 31-Nov. 3, 1996, vol. 1, pp. 185-186.

Matsuki et al., Signal Transmission for Implantable Medical Devices using Figure-of-eight Coils, IEEE Transactions on Magnetics, vol. 32 No. 5, pp. 5121-5123, Sep. 1996.

Melvin, D.B., et al., Electric Power Induction Through an Isolated Intestinal Pouch. (1991) Trans. Am. Soc. Intern. Organs, vol. XXXVII;M203-M204.

Miller et al. Development of an Autotuned Transcutaneous Energy Transfer System. ASAIO Journal. 1993;39:M706-M710.

Mitamura et al. Development of an Implantable Motor-Driven Assist Pump System. IEEE Transactions on Biomedical Engineering. vol. 37(2), pp. 146-156, 1990.

Mitamura et al. A Transcutaneous Optical Information Transmission System for Implantable Motor-drive Artificial Hearts. ASAIO Transactions.1990;36:M278-M280.

Mohammed et al. A miniature DC-DC converter for energy producing implantable devices. IEEE Ninth Annual Conference of the Engineering in Medicine and Biology Society, 1147-1148, 1987.

Mohammed, Design of radio frequency powered coils for implantable stimulators. IEEE Ninth Annual Conference of the Engineering in Medicine and Biology Society, 1378-1379, 1987.

Mussivand et al. Remote energy transmission for powering artificial hearts and assist devices. Artificial Heart 6/6th International Symposium on Artificial Heart and Assist Devices. Akutsu et al., eds., Springer-Verlag, Tokyo, pp. 344-347, 1998.

Mussivand et al. Transcutaneous energy transfer system performance evaluation. Artificial Organs. May 1993;17 (11):940-947.

Myers et al. A transcutaneous power transformer. Transactions of the American Society for Artificial Internal Organs, vol. 14, pp. 210-214, 1968.

Phillips, R.P., A High Capacity Transcutaneous Energy Transmission System. ASAIO Journal, vol. 41: M259-M262 (1995).

Rintoul et al, Continuing Development of the Cleveland Clinic-Nimbus Total Artificial Heart. ASAIO Journal, 39: M168-171 (1993).

Rosenberg et al., Progress Towards a Totally Implantable Artificial Heart. Cardiovascular Science & Technology: Basic & Applied, I. Precised Proceedings, pp. 214-216 (1989-1990).

(56) References Cited

OTHER PUBLICATIONS

Sherman et al., Energy Transmission Across Intact Skin for Powering Artificial Internal Organs. Trans. Am. Soc. Artificial Intern Organs, vol. XXVII, 1981, pp. 137-141.

Sherman et al., Transcutaneous energy transmission (TET) system for energy intensive prosthetic devices. Progress in Artificial Organs. 1985;400-404.

Sutton, A miniaturized device for electrical energy transmission through intact skin-concepts and sesults of initial tests. Third Meeting of the International Society for Artificial Organs. vol. 5, abstracts, Jul. 1981, pp. 437-440.

Weiss et al. A telemetry system for the implanted total artificial heart and ventricular assist device. IEEE Ninth Annual Conference of the Engineering in medicine and Biology Society, pp. 186-187, 1987.

Weiss et al., Permanent Circulatory Support at the Pennsylvania State University. IEEE Transaction on Biomedical Engineering 37(2):138-145 (Feb. 1990).

* cited by examiner

TRANSCUTANEOUS ENERGY TRANSFER SYSTEM WITH MULTIPLE SECONDARY COILS

RELATED APPLICATIONS

This application claims priority to U.S. Provisional Application Ser. No. 61/425,159, filed on Dec. 20, 2010, and entitled "Transcutaneous Energy Transfer System with Multiple Secondary Coils."

FIELD

The invention relates to transcutaneous energy transfer (TET) devices and more particularly to an improved secondary coil system for such devices which provides a patient with multiple primary coil coupling locations for redundancy and comfort.

BACKGROUND

Many medical devices adapted for implantation also have high power requirements and must be frequently connected to external power sources. Inductively coupled transcutaneous energy transfer (TET) systems are increasingly popular for use in connection with these high-power implantable devices. A TET system may be employed to supplement, replace, or charge an implanted power source, such as a rechargeable battery. Unlike other types of power transfer systems, TET systems have an advantage of being able to provide power to the implanted electrical and/or mechanical device, or recharge the internal power source, without puncturing the skin. Thus, possibilities of infection are reduced and comfort and convenience are increased.

TET devices include an external primary coil and an implanted secondary coil, separated by intervening layers of tissue. The primary coil is designed to induce alternating current in the subcutaneous secondary coil, typically for transformation to direct current to power an implanted device. TET devices therefore also typically include an oscillator and other electrical circuits for periodically providing appropriate alternating current to the primary coil. These circuits typically receive their power from an external power source.

Generally, the non-implanted portions of conventional TET systems are attached externally to the patient, typically by a belt, adhesive, or other fastener, such that the primary coil of the TET is operationally aligned with the implanted secondary coil. Such a configuration can be disadvantageous, however, particularly when only one attachment point is available. For example, connecting the primary coil of a conventional TET system to the same patch of skin for every charge can cause significant irritation at the attachment site. In addition, movements of the patient may alter the position of the primary coil so that it is not properly positioned over the implanted secondary coil to achieve a desired or required transfer of power. This is especially problematic during sleep, when a patient's unconscious movements in bed may move the primary coil out of alignment with the secondary coil. As a result, patients with conventional TET systems must often remain in a particular orientation when resting to avoid unintentionally disconnecting the primary coil.

Furthermore, should a patient's implanted TET system experience a component failure in the secondary coil, which can happen due to wire flex, electrical short, or introduction of a foreign object like a hypodermic needle, emergency surgery must be conducted before the implanted battery exhausts its charge. Such emergency surgeries pose serious risks to patients who require TET systems to survive.

SUMMARY

To overcome the above and other drawbacks of conventional systems, the present invention provides a transcutaneous energy transfer system with a plurality of secondary coils that provides redundancy in the event of a system failure as well as an increase in patient comfort.

One aspect of the invention provides a plurality of secondary coils to receive transcutaneous energy, at least one primary coil configured to transmit transcutaneous energy to the secondary coils, a controller, and a charge storage device. The plurality of secondary coils, controller, and charge device are adapted for disposition in a patient. The controller includes circuitry to isolate the secondary coils from each other and direct electric current from at least one of the secondary coils to charge the charge storage device.

In one embodiment, the secondary coils are isolated from each other using electrical diodes. In another embodiment, the system includes a controller to select one of the secondary coils for energy transfer and to electrically decouple the other secondary coils.

In a further embodiment, the system includes an alarm to alert a patient in the event of a failure of one ore more of the secondary coils.

For example, the system can include a first secondary coil and a second secondary coil adapted for disposition in a patient's body. In one embodiment, the first secondary coil is adapted for disposition in the left side of a patient's body, and the second secondary coil is adapted for disposition in the right side of a patient's body. In some embodiments, the system can also include a first primary coil and a second primary coil configured to simultaneously transmit transcutaneous energy to the first and second secondary coils to decrease the time required to charge the storage device.

The system can also include a ventricular assist device or other implantable medical device connected to the controller.

The invention can be implemented as part of an implantable device having a plurality of secondary coils disposable in a patient, a control circuitry, and an electric storage device. The plurality of secondary coils are adapted to produce an electric current in the presence of a time-varying magnetic field and the control circuitry isolates the secondary coils from each other and directs electric current from at least one of the secondary coils to the electric storage device.

In one embodiment, the control circuitry is further configured to select one of the secondary coils for energy transfer and electrically decouple the other secondary coils. In another embodiment, the secondary coils are isolated from each other using electrical diodes. In still another embodiment, the controller can select the coil with the best coupling for energy transfer.

In a further embodiment, the device also includes an alarm to alert a patient in the event of a failure of one or more of the secondary coils.

In still another embodiment, the device includes a first secondary coil and a second secondary coil adapted for disposition in a patient's body. In another embodiment, the first secondary coil is adapted for disposition in the left side of a patient's body and the second secondary coil is adapted for disposition in the right side of a patient's body.

In yet another embodiment, the device also includes a ventricular assist device connected to the control circuitry.

BRIEF DESCRIPTION OF THE DRAWINGS

The invention will be more fully understood from the following detailed description taken in conjunction with the accompanying drawings, in which.

DETAILED DESCRIPTION

Figure 1:
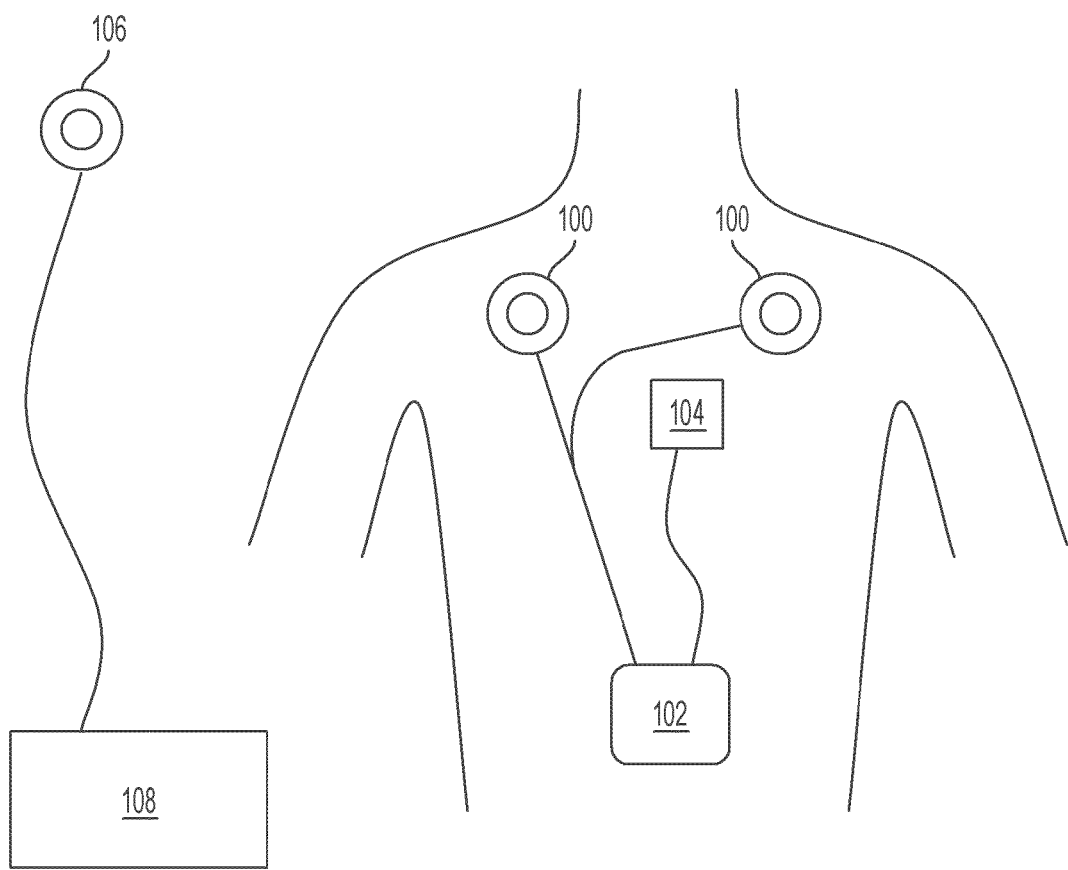
FIG. 1 is a diagram of a TET system of the present invention.

Certain exemplary embodiments will now be described to provide an overall understanding of the principles of the devices disclosed herein. One or more examples of these embodiments are illustrated in the accompanying drawings. Those skilled in the art will understand that the devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A transcutaneous energy transfer (TET) system works by inductively coupling a primary coil to a secondary coil. The primary coil, configured for disposition outside a patient, is connected to a power source and creates a time-varying magnetic field. When properly aligned with a secondary coil, the time-varying magnetic field from the primary coil induces an alternating electric current in the secondary coil. The secondary coil is configured for implantation inside a patient and can be connected to a controller that harnesses the electric current and uses it to, for example, charge a battery pack or power an implantable device like a ventricular assist device (VAD), or other cardiac assist device. By utilizing induction to transfer energy, TET systems avoid having to maintain an open passage through a patient's skin to power an implantable device.

Prior art TET systems feature a single secondary coil that is usually implanted under a patient's skin near the chest. To properly align the primary and secondary coils, the primary coil is typically placed directly over the secondary coil on the patient's chest. The primary coil is secured to the patient using any of several mechanical fastening mechanisms including belts, straps, adhesives, or magnetic coupling via permanent magnets.

A problem commonly encountered with prior art TET systems is that a patient is forced to remain in a particular position when the primary coil is attached because moving to a different position may result in the primary coil being bumped out of alignment with the secondary coil. For example, a patient with a secondary coil implanted on the right side of their chest would have to sleep on their left side to avoid bumping the primary coil out of position.

In addition, prior art TET systems require a near constant supply of energy from the primary coil module, meaning that a patient spends almost all of their time with the primary coil attached to their skin. If the primary coil is always attached in the same location, severe irritation and discomfort can result due to constant contact, local heat, sweat, etc.

Beyond skin irritation, prior art TET systems provide no long term redundancy in the event that an implanted secondary coil experiences a catastrophic failure. Failure of an implanted secondary coil requires emergency surgery to replace the coil before the implanted battery exhausts itself.

The present invention solves these problems by providing a TET system having a plurality of secondary coils configured to be implanted in a patient at different locations. Such a configuration allows a patient to connect the primary coil to a different region of their body and thereby allow different resting positions while preventing any one area from becoming overly irritated. Additionally, and as is discussed in more detail below, the present invention provides redundancy in case any of the plurality of secondary coils should fail because each coil is electrically isolated from the others and a patient can simply switch to a different secondary coil in the event of a failure. Furthermore, the present invention allows the connection of multiple primary coils to speed the replenishment of a charge storage device, given that the energy transfer per secondary coil is limited by the maximum temperature rise threshold.

FIG. 1 shows a diagram of an exemplary TET system of the present invention. An implantable device comprises a plurality of secondary coils 100 adapted for disposition in a patient. The secondary coils are connected to a controller 102 that is adapted to receive electric current from the plurality of secondary coils for use or storage. The controller can then direct the electric current to, for example, charge a battery (which can be integrated with controller 102) or power a ventricular assist device 104 or other implantable device.

FIG. 1 also shows an exemplary embodiment of primary coil 106 that is adapted to remain outside the body and transfer energy inductively to the secondary coils. Primary coil 106 is connected to an external power source, which can include, for example, conditioning and control circuitry. Optionally, more than one primary coil 106 can be used simultaneously with the multiple secondary coils 100 to reduce the time required to charge an implanted battery. If multiple primary coils 106 are attached, the system can receive energy from any or all of the primary coils. The system can also direct energy to a subset of the attached coils in order to maximize efficiency. For example, if one of the primary coils 106 is knocked out of alignment, power can be directed to the primary/secondary coil pair with the best coupling efficiency, thereby maximizing the efficiency of the overall system.

In use, primary coil(s) 106 are placed in proximity to one or more secondary coils 100 such that they are substantially in axial alignment. Power source 108, which can include conditioning circuitry to produce a desired output voltage and current profile, is then activated to produce a time-varying magnetic field in the primary coil(s) 106. The time-varying magnetic field induces an electric current to flow in the secondary coils 100 and the current is subsequently distributed to controller 102 and any attached ventricular assist devices 104 or charge storage devices.

Figure 2:
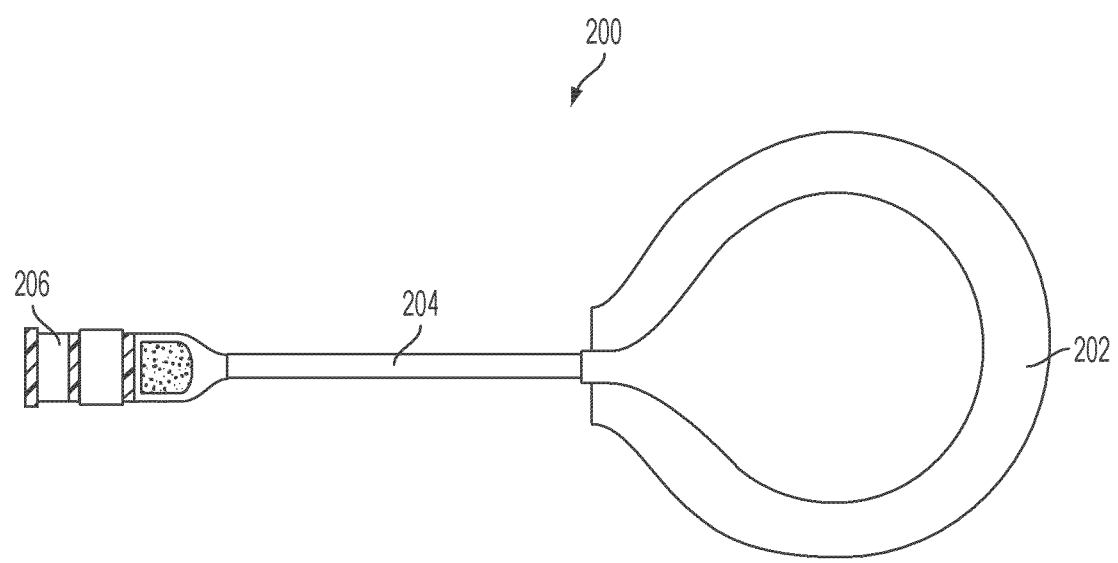
FIG. 2 is an illustration of an exemplary implantable secondary coil.

FIG. 2 illustrates an exemplary secondary coil 200 adapted for disposition in a patient. Secondary coil 200 features a coil portion 202 consisting of several turns of conductive wire, a connecting portion 204, and an optional interface portion 206. Coil portion 202 can vary in size and turns of wire depending on numerous factors such as the intended implantation site. In an exemplary embodiment, coil portion 202 comprises 12 turns of Litz wire in a two-inch diameter coil. In addition to the wire, the coil 202 can contain a ferrous core and electronic circuitry which rectifies the AC current and communicates with the external coil and driver to provide a regulated DC output voltage. An exemplary secondary coil is described in U.S. Patent Pub. No. 2003/0171792, which is hereby incorporated by reference in its entirety.

The coil portion 202 is electrically coupled to the connecting portion 204, which can be formed from a segment of the same wire used to form the coil portion. The length of connecting portion 204 can also vary based on, for example, the distance from the implantation site of a secondary coil to that of a controller.

Connecting portion 204 is also electrically coupled to optional interface portion 206. Interface portion 206 is used to connect the secondary coil 200 to a controller 102. The interface portion can include any electrical connector known in the art to facilitate modular connection to a controller 102, or can consist of a terminal end of the connecting portion 204 that is capable of being electrically connected to a controller.

One advantage of the present invention is that the plurality of secondary coils may be adapted for disposition anywhere in a patient. In an exemplary embodiment, two secondary coils are included that are adapted for disposition in a patient's left and right chest area. Such a configuration minimizes the invasiveness of implanting the coils while providing all of the benefits of varied coupling location and electrical redundancy.

Figure 3:
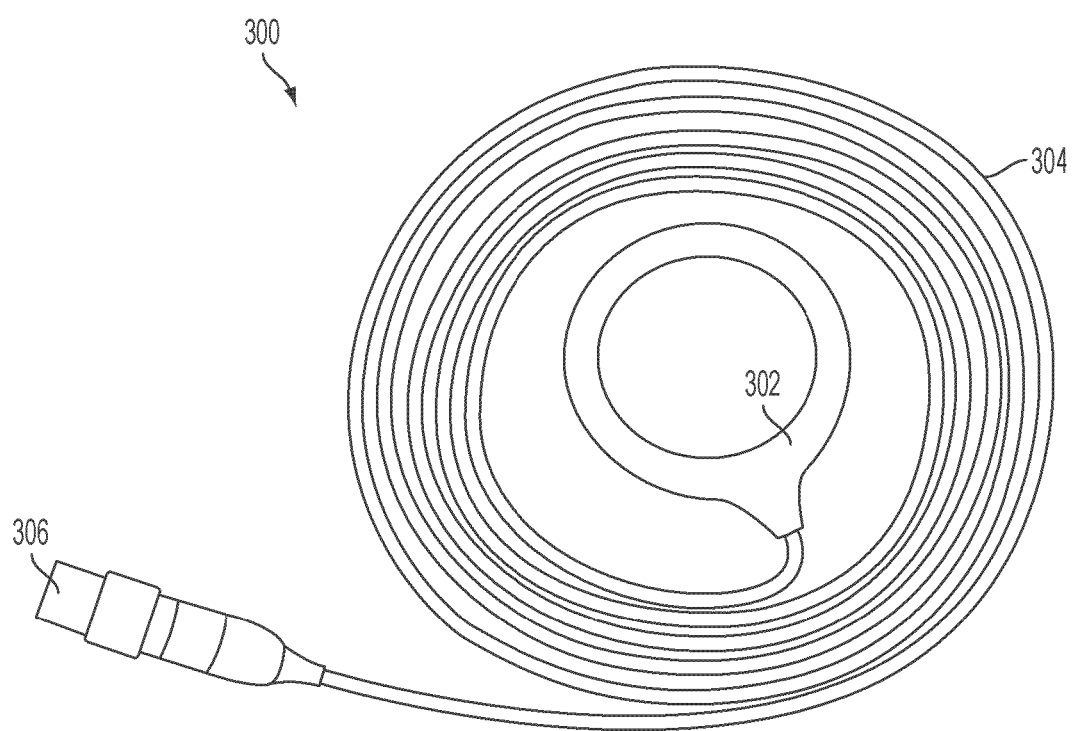
FIG. 3 is an illustration of an exemplary primary coil.

FIG. 3 shows an exemplary primary coil 300 configured to transmit transcutaneous energy to a secondary coil like that illustrated in FIG. 2. Similar to secondary coil 200 in FIG. 2, primary coil 300 can include a coil portion 302, a connecting portion 304, and an interface portion 306. Primary coil 300 is adapted for disposition outside the patient, however, and induces electric current in secondary coil 200 by emitting a time-varying magnetic field from coil portion 302. The opening at the center of the primary coil 300 can be used to overlay the portion of the secondary coil 200 that protrudes under the skin of the patient to improve primary and secondary coil alignment, thereby improving coupling efficiency.

Coil portion 302 can vary in size and turns of wire depending on several factors including, for example, the size of any secondary coils it will be used with. Coil portion 302 is electrically coupled to connecting portion 304. Connecting portion 304 can be formed from a portion of the wire used to form coil portion 302. Connecting portion 304 can vary in length depending on any of several factors including, for example, how far a patient is from a power source. Connecting portion 304 is in turn electrically coupled to interface portion 306, which is adapted to connect to a power source (or associated conditioning or control circuitry) like power source 108 of FIG. 1. Interface portion 306 can include any electrical connector known in the art to facilitate modular connections to external power source 108, or can consist of a terminal end of connecting portion 304 that is adapted to be electrically connected to power source 108.

Figure 4:
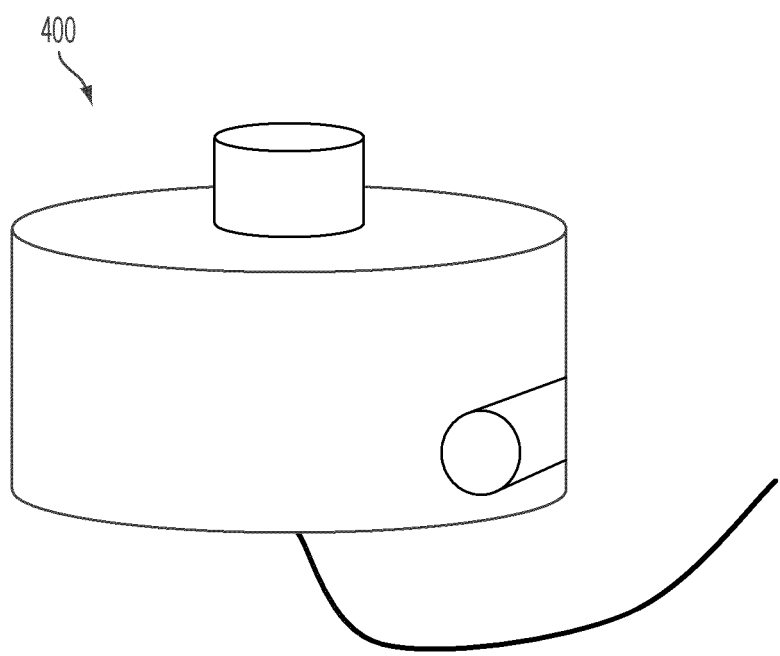
FIG. 4 is a front perspective view of an exemplary ventricular assist device powered by a TET system.

Primary coil 300 is used to transfer power transcutaneously in order to ultimately support an implantable device like the ventricular assist device (VAD) 400 depicted in FIG. 4. The ventricular assist device 400 aids the heart in circulating blood through the body. The integration of sufficient battery capacity within the body and a power-efficient assist device (5-6 Watt electrical input) can allow a patient to be mobile without any external power source or primary coil attachment for long periods of time. This, along with the shortened charge times achieved with the use of multiple primary coils for power transfer, results in an unsurpassed quality of life for patients using these systems.

While a ventricular assist device is an exemplary embodiment of an implantable device that can benefit from TET systems like the present invention, it is by no means the only implantable device that can be powered in this way. Other cardiac assist devices, as well as many other types of powered implantable devices, can be used with the system of the present invention.

Figure 5:
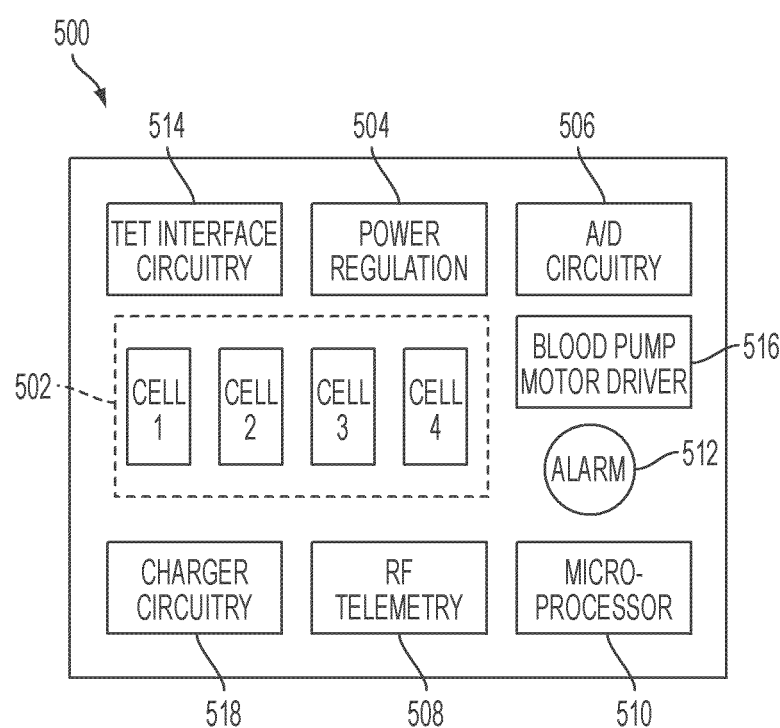
FIG. 5 is a diagram of an exemplary implantable controller containing power and control circuitry, as well as a rechargeable battery pack.

FIG. 1 shows the secondary coils 100 connected to the ventricular assist device 104 via a controller like that illustrated in FIG. 5. FIG. 5 depicts an integrated controller and battery pack 500 that is adapted for disposition in a patient. The rechargeable battery pack includes battery cells 502 that can be charged using the electric current received from the secondary coil(s) 100. Electric current received from the secondary coil(s) 100 is processed through the TET interface circuitry 514 and conditioned for use with the battery cells 502 through the charger circuitry 518 or to power the internal electronics and ventricular assist device 104 by power regulation circuitry 504. Power regulation circuitry 504 can contain any of several circuit designs known in the art that are effective to convert the voltage and current received from the TET interface circuitry 514 into a desired output voltage and current that can be used to power the internal electronic circuitry 506, 508, 510, 512 and the ventricular assist device 104 via the blood pump motor driver 516.

The TET interface circuitry 514 can also incorporate circuitry designed to prevent a failure or electrical short in any one secondary coil from affecting the operation of controller 500 or VAD 104. For example, the diodes or Ideal Diodes 602 shown in FIG. 6 can be used to prevent system voltage drops or current backflow to an individual secondary coil 100 from the controller 102 or any other secondary coil. Such system failures can be caused by a component failure in an individual secondary coil, such as wire failure due to flexing or external interference from, for example, a hypodermic needle or moisture ingress that causes electro-corrosion.

Alternatively, TET interface circuitry 514 can include additional controller circuitry allowing it to electrically decouple any secondary coils not in use. In such an embodiment, the controller circuitry can be configured to select one or more secondary coils receiving energy from primary coils for use in charging an implanted battery or other charge storage device. One of skill in the art will appreciate that any of several circuit designs can implement this selective coupling feature, including varying voltage and/or current supply for both secondary coils if operated in parallel.

Figure 6:
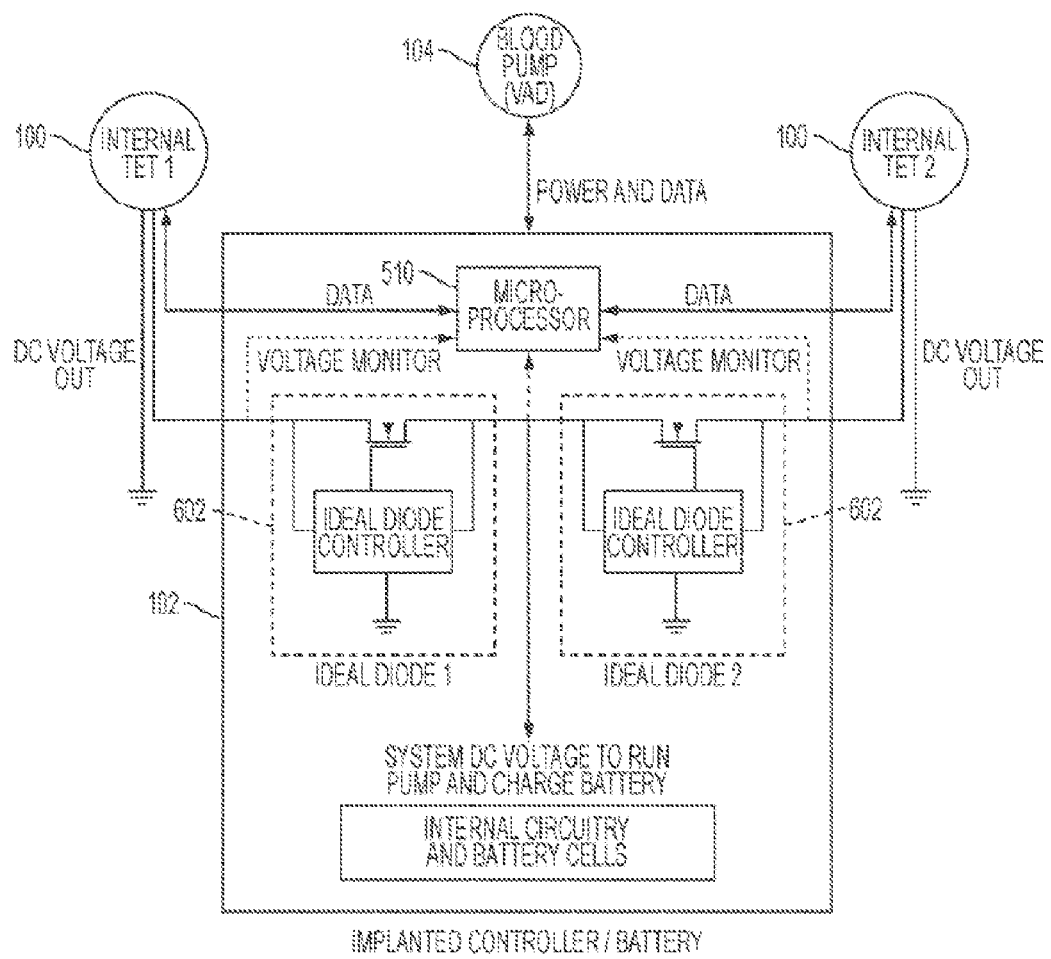
FIG. 6 is a circuit diagram of the implantable device illustrated in FIG. 1.

FIG. 6 illustrates an exemplary circuit diagram for the implantable device shown in FIG. 1, in which two secondary coils 100 are connected to the implanted controller and battery 102. Each of the secondary coils 100 provides a regulated DC voltage to the implanted controller 102 when coupled to the primary coil 106. The DC voltage from each secondary coil 100 is fed through an ideal diode circuit 602 within the TET interface circuitry 514. The ideal diode circuit 602 behaves like a standard diode with the exception a very low forward voltage drop. This is accomplished by switching a field-effect transistor (FET) on or off based on the voltage detected at the anode and cathode of the circuit.

Unlike a Schottky diode, which has a forward voltage drop between 0.3 and 0.5 volts, the ideal diode has a forward voltage drop of less than 0.1 volts. The lower voltage drop reduces the power dissipated in the diode, allowing more power to be available for running the VAD 104 and charging the battery. In addition, there is less heat generated in the ideal diode due to the lower power loss. The greater efficiency of the ideal diodes also allows externally carried batteries (which can be used as power source 108) to be smaller, thereby increasing patient quality of life.

The ideal diodes 602 are connected in an "OR" configuration, allowing one or both secondary coils 100 to source the power to the internal controller 102. Like a Schottky diode, the ideal diode will only conduct current in the forward direction. In the event of a fault, which puts a low impedance, or short, across the DC voltage output of one of the secondary coils 100, the ideal diode 602 will prevent the fault from drawing down the system voltage. Reduction of the system voltage could otherwise lead to stoppage of the VAD 104 and a serious threat to a patient's life. With the diodes shown in FIG. 6, the system can still function on the other secondary coil 100, eliminating the need for emergency surgery to replace the faulty secondary coil before the internal battery 502 runs down.

Returning to FIG. 5, controller 500 can also include VAD circuitry 506 and 516 that is configured to control the ventricular assist device 104. The VAD circuitry can include monitoring features so that any failures in the ventricular assist device 104 are detected in the controller 500. The controller 500 can further include a central processor 510 that coordinates functions executed by the Charger Circuitry 518, power regulation circuitry 504, Blood Pump Motor Driver Circuitry 516, and A/D circuitry 506.

The processor 510 also monitors the function of secondary coils 100 and ventricular assist device 104. If a fault is detected in either component, processor 510 can utilize RF telemetry module 508 to allow it to communicate fault information with a user via an external display or control console. The display or control console could take the form of a common desktop computer, mobile phone, PDA, bed-side control console, or any other type of computing or signaling device known in the art. The fault information communicated to a user can also be in the form of an alarm sounded by a display or control console as described above. Alternatively, controller 500 can include an alarm module 512 that can sound an auditory or vibratory alarm in the event of a failure. In addition, the external power source 108 can also be configured to detect a fault in a coupled secondary coil 100, alert a patient accordingly, and guide a user to an optimal position of the primary coil.

The system of the present invention provides several benefits over prior art TET systems. For example, the present invention provides redundancy in the event of secondary coil failure. In prior art TET systems, failure of a secondary coil requires emergency surgery to replace the coil before the implanted battery pack exhausts its charge. With the TET system of the present invention, however, a patient can avoid emergency surgery by utilizing another secondary coil until the failed coil can be replaced. This is made possible by the electrical isolation of each of the plurality of secondary coils connected to the controller. Another advantage of the present invention is increased patient comfort. Enabling a patient to attach a primary coil on either side of their body, to alternate coupling locations when the skin over one secondary coil becomes irritated, and to use multiple primary coils to speed battery charging time provides an increase in patient comfort and quality of life.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A transcutaneous energy transfer system, comprising:
   a plurality of secondary coils comprising a first secondary coil and a second secondary coil, said first and second secondary coils adapted for disposition in a patient to receive transcutaneous energy;
   first and second primary coils configured to simultaneously transmit transcutaneous energy to one of the first and second secondary coils; and
   a controller, also adapted for disposition in the patient, comprising circuitry to isolate the first and second secondary coils from each other while also allowing each of the first and second secondary coils to simultaneously charge a storage device and/or power an implantable medical device when each of the first and second secondary coils is simultaneously coupled to the first and second primary coils, respectively.

2. The system of claim 1, wherein the controller further comprises circuitry to select one of the first and second secondary coils for energy transfer and electrically decouple the other of the first and second secondary coils.

3. The system of claim 1, wherein the system further comprises an alarm to alert the patient in an event of a failure of one or more of the secondary coils.

4. The system of claim 1, wherein the plurality of secondary coils are connected using diodes, Ideal Diodes, or switches.

5. The system of claim 1, wherein the first secondary coil is adapted for disposition in a left side of the patient's body and the second secondary coil is adapted for disposition in a right side of the patient's body.

6. The system of claim 1, wherein the first primary coil and the second primary coil are configured to simultaneously transmit transcutaneous energy to the first and second secondary coils to decrease a time required to charge the storage device.

7. The system of claim 1, wherein the system further comprises a ventricular assist device, or implantable medical device connected to the controller.

8. The system of claim 1, wherein the controller selects one of the first and second secondary coils with a best coupling for energy transfer.

9. An implantable device, comprising:
   first and second secondary coils disposable in a patient and adapted to produce an electric current in a presence of a time-varying magnetic field; and
   a control circuitry to isolate the first and second secondary coils from each other while also directing electric current from both of the secondary coils to an electric storage device and/or an implantable medical device when each of the secondary coils is simultaneously coupled to a first and a second primary coil, respectively.

10. The device of claim 9, wherein the control circuitry is further configured to select one of the first and second secondary coils for energy transfer and electrically decouple the other of the first and second secondary coils.

11. The device of claim 10, wherein the control circuitry is further configured to select one of the first and second secondary coils with a best coupling for energy transfer.

12. The device of claim 9, wherein the device further comprises an alarm to alert the patient in an event of a failure of one or more of the secondary coils.

13. The device of claim 9, wherein the first and second secondary coils are isolated using diodes.

14. The device of claim 9, wherein the first secondary coil is adapted for disposition in a left side of the patient's body and the second secondary coil is adapted for disposition in a right side of the patient's body.

15. The device of claim 9, wherein the device further comprises a ventricular assist device or implantable medical device connected to the control circuitry.

* * * * *